United States Patent
Watanabe et al.

(10) Patent No.: US 6,930,076 B2
(45) Date of Patent: Aug. 16, 2005

(54) NEMATICIDAL TRIFLUOROBUTENYL IMIDAZOLE THIOETHER DERIVATIVES

(75) Inventors: Yukiyoshi Watanabe, Tochigi (JP); Koichi Ishikawa, Tochigi (JP); Yuichi Otsu, Tochigi (JP); Katsuhiko Shibuya, Tochigi (JP); Takahisa Abe, Hokkaido (JP)

(73) Assignee: Bayer CropScience AG, Monheim (DE)

(*) Notice: Subject to any disclaimer, the term of this patent is extended or adjusted under 35 U.S.C. 154(b) by 0 days.

(21) Appl. No.: 10/498,175
(22) PCT Filed: Dec. 2, 2002
(86) PCT No.: PCT/EP02/13608
§ 371 (c)(1),
(2), (4) Date: Nov. 22, 2004
(87) PCT Pub. No.: WO03/049541
PCT Pub. Date: Jun. 19, 2003

(65) Prior Publication Data
US 2005/0080123 A1 Apr. 14, 2005

(51) Int. Cl.[7] ............ A01N 43/50; C07D 233/84; C07D 233/32; C07D 233/70; C07D 233/30
(52) U.S. Cl. ............ 504/277; 514/386; 548/316.4; 548/322.5; 548/324.1; 548/325.1
(58) Field of Search ............ 548/316.4, 322.5, 548/324.1, 325; 504/277; 514/386

(56) References Cited

U.S. PATENT DOCUMENTS 3,513,172 A   5/1970   Brokka .................. 260/302
4,952,580 A   8/1990   Martinez et al. ......... 514/236.2

FOREIGN PATENT DOCUMENTS

GB   2293380        3/1996
WO   95/04727       2/1995
WO   95/24403       9/1995

OTHER PUBLICATIONS

J. Amer. Chem., vol. 71, Feb. 1949, pp. 644–646, Reuben G. Jones, "Studies on Imidazoles. II. The Synthesis of 5-Imidazolecrboxylates from Glycine and Substituted Glycine Esters".

J. Amer. Chem., vol. 71, Dec. 1949, pp. 4000–4002, Reuben G. Jones et al, Studies on Imidazoles. IV. The Synthesis and Antithyroid Activity of Some 1-Substituted-2-mercaptoimidazoles.

*Primary Examiner*—Alton Pryor
(74) *Attorney, Agent, or Firm*—Richard E.L. Henderson

(57) ABSTRACT

The present invention relates to novel trifluorobutenyl imidazole thioether derivatives of the following formula (I)

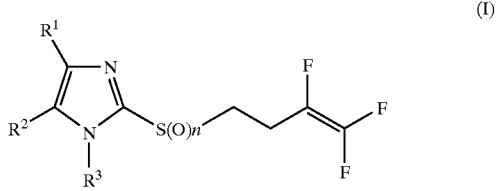

wherein
$R^1$ represents hydrogen or halogen,
$R^2$ represents hydrogen, halogen or alkoxycarbonyl,
$R^3$ represents hydrogen, alkyl, alkenyl, cycloalkyl or aralkyl, and
n represents 0,1 or 2,
with the proviso that $R^1$, $R^2$ and $R^3$ do not all represent hydrogen at the same time,
to a process for their preparation and to their use as nematicides.

7 Claims, No Drawings

NEMATICIDAL TRIFLUOROBUTENYL IMIDAZOLE THIOETHER DERIVATIVES

The present patent application has been filed under 35 U.S.C. 371 as a national stage application of PCT/EP02/13608, filed Dec. 2, 2002, which was published in English as International Patent Publication WO 03/049541 on Jun. 19, 2003, which is entitled to the right of priority of Japanese Patent Application JP 2001-380152, filed Dec. 13, 2001.

The present invention relates to novel trifluorobutenyl imidazole thioether derivatives, to processes for their preparation and to their use as nematicides.

U.S. Pat. No. 3,513,172 describes that certain kinds of trifluorobutenyl compounds have a nematicidal activity and Japanese Laid-open Patent Publication No. 500037/1988 describes that certain kinds of polyhaloalkene compounds can be used as nematicides. Further, in the British Laid-open Patent Publication No. 2,293,380 certain kinds of heterocyclic compounds are described as having a nematicidal activity. WO 95/24403 also describes 4,4-difluorobutenyl compounds with a nematicidal activity. WO 95/4727 finally describes preparation processes for nematicidal fluoroalkenyl thioheterocyclic derivatives.

There have now been found novel trifluorobutenyl imidazole thioether derivatives of the following formula (I)

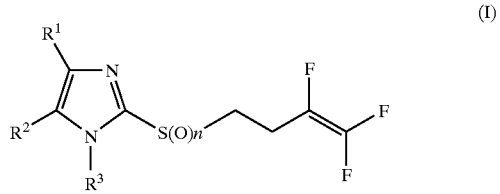

(I)

wherein
$R^1$ represents hydrogen or halogen,
$R^2$ represents hydrogen, halogen or alkoxycarbonyl,
$R^3$ represents hydrogen, alkyl, alkenyl, cycloalkyl or aralkyl, and
n represents 0,1 or 2,
with the proviso that $R^1$, $R^2$ and $R^3$ do not all represent hydrogen at the same time.

Preferred meanings of the substituents $R^1$, $R^2$, $R^3$ are given below.

$R^1$ preferably represents hydrogen, fluoro, chloro or bromo.

$R^2$ preferably represents hydrogen, fluoro, chloro, bromo, methoxycarbonyl, e-thoxycarbonyl, n- or i-propoxycarbonyl, n-, i-, s- or t-butoxycarbonyl.

$R^3$ preferably represents hydrogen, $C_{1-6}$-alkyl, $C_{3-4}$-alkenyl, $C_{3-6}$-cycloalkyl or benzyl.

$R^1$ particularly preferably represents hydrogen, chloro or bromo.

$R^2$ particularly preferably represents hydrogen, chloro, bromo, methoxycarbonyl, ethoxycarbonyl or n-propoxycarbonyl.

$R^3$ particularly preferably represents hydrogen, methyl, ethyl, n-propyl, isopropyl, n-butyl, sec-butyl, tert-butyl, n-pentyl, allyl, 2-butenyl, cyclopropyl, cyclopentyl, cyclohexyl or benzyl.

The compounds of the above-mentioned formula (I) can be synthesised, for example, by the following preparation processes (a), (b) or (c):

Preparation Process (a)

The novel compounds of the formula (I) wherein n represents 0 are obtained when compounds of the formula (II)

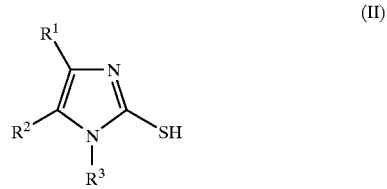

(II)

wherein
$R^1$, $R^2$ and $R^3$ have the afore mentioned definition,
are reacted with 4-bromo-1,1,2-trifluoro-1-butene in the presence of insert solvents, and, if appropriate, in the presence of an acid binder.

Preparation Process (b)

The novel compounds of the formula (I) wherein n represents 1 or 2 are obtained when compounds of the formula (Ia)

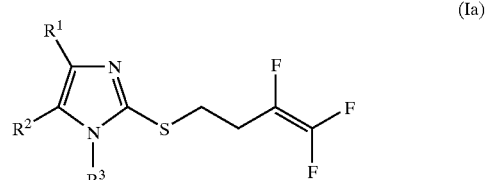

(Ia)

wherein
$R^1$, $R^2$ and $R^3$ have the aforementioned definition,
are oxidised in the presence of inert solvents.

Preparation Process (c)

The novel compounds of the formula (I) wherein $R^1$ represents hydrogen, $R^2$ represents halogen and n represents 0, or wherein $R^1$ and $R^2$ represent halogen and n represents 0 are obtained when compounds of the formula (Ib)

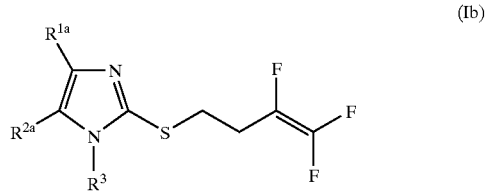

(Ib)

wherein
$R^{1a}$ and $R^{2a}$ each represent hydrogen and $R^3$ has the aforementioned definition,
are reacted with a halogenating agent in the presence of inert solvents.

The compounds of the formula (I) of the present invention show a strong nematicidal activity and a good compatibility with various crops.

The compound s of the formula (I) according to the present invention surprisingly show a significantly better nematicidal activity compared with the compounds described in the aforementioned state of the art.

In the present specification "halogen" represents fluoro, chloro, bromo or iodo, preferably represents fluoro, chloro or bromo and particularly preferably represents chloro or bromo.

"Alkyl" as well as the alkyl part of "alkoxycarbonyl" represents a straight-chain or branched-chain alkyl such as methyl, ethyl, n-or iso-propyl, n-, iso-, sec- or tert-butyl, n-pentyl, n-hexyl, n-heptyl, n-octyl etc., preferably represents $C_{1-8}$-alkyl, more preferably represents, $C_{1-6}$-and particularly preferably represents $C_{1-4}$-alkyl.

"Alkenyl" represents alkenyl such as vinyl, allyl, 1-propenyl, 1-, 2- or 3-butenyl etc., preferably represents $C_{3-4}$-alkenyl and particularly preferably represents alkyl or 2-butenyl.

"Cycloalkyl" represents cycloalkyl such as cyclopropyl, cyclobutyl, cyclopentyl, cyclohexyl, cycloheptyl, cyclooctyl etc., preferably represents $C_{3-6}$-cycloalkyl, and particularly preferably represents cyclopropyl, cyclopentyl or cyclohexyl.

"Aralkyl" represents $C_{7-12}$(total carbon number)-aralkyl, wherein the aryl part is phenyl or naphthyl and wherein the alkyl part is methyl or ethyl, such as benzyl, phenethyl, α-methylbenzyl, α- or β-naphthylmethyl, α- or β-naphthylethyl etc. and preferably represents benzyl.

Preferred compounds according to the present invention are compounds of the formula (I) wherein $R^1$ represents hydrogen, fluoro, chloro or bromo, $R^2$ represents hydrogen, fluoro, chloro, bromo, methoxycarbonyl, ethoxycarbonyl, n- or i-propoxycarbonyl, n-, i-, s- or t-butoxycarbonyl, $R^3$ represents hydrogen, $C_{1-6}$-alkyl, $C_{3-4}$-alkenyl, $C_{3-6}$-cycloalkyl or benzyl, and n represents 0,1 or 2, with the proviso that $R^1$, $R^2$ and $R^3$ do not all represent hydrogen at the same time.

Particularly preferred compounds according to the present invention are compounds of the formula (I) wherein $R^1$ represents hydrogen, chloro or bromo, $R^2$ represents hydrogen, chloro, bromo, methoxycarbonyl, ethoxycarbonyl or n-propoxycarbonyl, $R^3$ represents hydrogen, methyl, ethyl, n-propyl, isopropyl, n-butyl, sec-butyl, tert-butyl, n-pentyl, allyl, 2-butenyl, cyclopropyl, cyclopentyl, cyclohexyl or benzyl, and n represents 0,1 or 2, with the proviso that $R^1$, $R^2$ and $R^3$ do not all represent hydrogen at the same time.

Using, for example, 2-mercapto-1-methylimidazole and 4-bromo-1, 1,2-trifluoro-1-butene as starting materials, the course of the reaction in the aforementioned process (a) can be illustrated by the following reaction scheme:

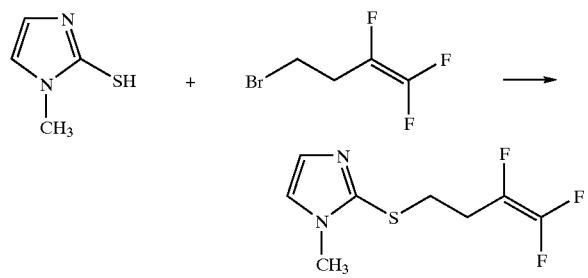

Using, for example, 1-methyl-2-(3',4',4'-trifluoro-3'-butenylthio) imidazole as starting materials and using, for example, m-chloroperbenzoic acid as oxidising agent, the course of the reaction in the aforementioned process (b) can be illustrated by the following reaction scheme:

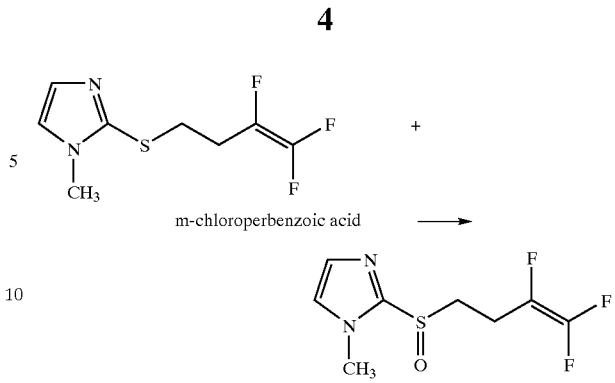

Using, for example, 1-methyl-2-(3',4',4'-trifluoro-3'-butenylthio) imidazole as starting materials and using, for example, N-chlorosuccinimide as halogenating agent, the course of the reaction in the aforementioned process (c) can be illustrated by the following reaction scheme:

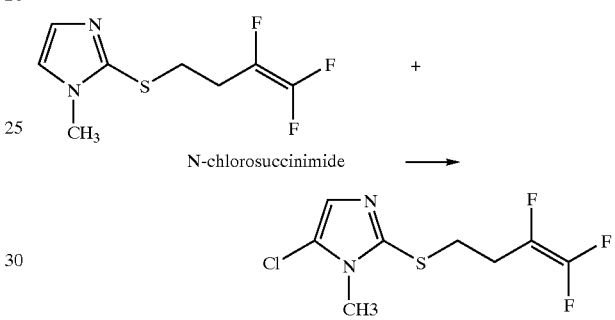

The compounds of the formula (II), used as starting materials in the aforementioned preparation process (a), include known compounds, described in, for example, *J. Amer. Chem.*, Vol. 71, p. 644–646, 1949 and, *J. Amer. Chem.*, Vol. 71, p. 4000–4002, 1949, or can be synthesised according to the processes described in said documents.

The following examples of the compounds of the formula (II) can be mentioned:
2-mercapto-1-methylimidazole, 1-ethyl-2-mercaptoimidazole, 2-mercapto-1-n-propylimidazole, 1isopropyl-2-mercaptoimidazole, 2-mercapto-1-n-butylimidazole, 2-mercapto-1-sec-butylimidazole, 2-mercapto-1-tert-butylimidazole, 1-cyclopropyl-2-mercaptoimidazole, 1-allyl-2-mercaptoimidazole, 1-benzyl-2-mercaptoimidazole, 5-methoxycarbonyl-2-mercapto-1-methylimidazole, 2-mercapto-1-methyl-5-n-propoxycarbonylimidazole, 5-ethoxycarbonyl-2-mercapto-1-methylimidazole etc.

4-Bromo-1,1,2-trifluoro-1-butene, used as starting material in the aforementioned preparation process (a), is a known compound described, for example, in WO 86/07590.

The compounds of the formula (Ia), used as starting materials in the aforementioned preparation process (b), correspond to the compounds of the formula (I) of the present invention wherein n represents 0. They can be synthesised, for example, according to the aforementioned preparation process (a).

Suitable oxidising agents which can be used for the oxidation of the compounds of the formula (Ia) in preparation process (b) are, in general, the customary oxidising agents which are used in the field of organic chemistry. They preferably include, for example, hydrogen peroxide water, m-chloroperbenzoic acid, peracetic acid, perbenzoic acid, magnesium monoperoxyphthalate, potassium peroxymonosulfate etc.

The compounds of the formula (Ib), used as starting materials in the aforementioned preparation process (c), correspond to the compounds of the formula (I) of the present invention wherein n represents 0. They can be synthesised, for example, according to the aforementioned preparation process (a).

Suitable halogenating agents, which can be used for reacting with the compounds of the formula (Ib) in the preparation process (c) are, in general, the customary halogenating agents which are used in the field of organic chemistry. They preferably include, for example, sulfuryl chloride, N-chlorosuccinimide, N-bromosuccinimide, trichloroisocyanuric acid, potassium fluoride, chlorine gas, bromine, iodine etc.

The reaction of the aforementioned preparation process (a) can be conducted in the presence of an adequate diluent. Diluents preferably used are, for example, aliphatic, alicyclic and aromatic hydrocarbons, such as, hexane, cyclohexane, petroleum ether, ligroine, benzene, toluene, xylene etc.; ethers, such as, diethyl ether, methyl ethyl ether, di-isopropyl ether, dibutyl ether, propylene oxide, dioxane, tetrahydrofuran etc.; ketones, such as, acetone, methyl ethyl ketone, methyl isobutyl ketone etc.; nitriles, such as acetonitrile, propionitrile, acryonitrile etc.; acid amides, such as, dimethylformamide, dimethylacetamide, N-methylpyrrolidone etc.

The reaction of the preparation process (a) can be conducted in the presence of an acid binder. Acid binder preferably used are, for example, hydroxides, carbonates and alcoholates etc. of alkali metals, tertiary amines, for example, triethylamine, diethylaniline, pyridine, 4-dimethylaminopyridine, 1,4-diazabicyclo[2,2,2]octane (DABCO), 1,8-diazabycyclo[5,4,0]undec-7-ene (DBU) etc.

When carrying out the process (a) according to the invention the reaction temperatures can be varied within a relatively wide range. In general, the process is carried out at temperatures between 0° C. and 180° C., preferably between 20° C. and 120° C. The process according to the invention is generally carried out under atmospheric pressure. However, it is also possible to carry out the process according to the invention under elevated or reduced pressure.

In preparation process (a) according to the invention, the compounds of the formula (I) can be obtained, for example, by reacting 0.8–1.5 moles of 4-bromo-1,1,2-trifluoro-1-butene with 1 mole of a compound of the formula (II) in a diluent, for example, acetonitrile, in the presence of 1–1.3 moles of an acid binder, for example, potassium carbonate, under refluxing.

The compounds of the formula (I) of the present invention which can be prepared by the preparation process (a) and wherein n, represents 0, $R^2$ represents alkoxycarbonyl and $R^3$ represents alkyl can be synthesised also according to another process described in Synthesis Example 5 below.

The reaction of the aforementioned preparation process (b) can be conducted in the presence of an adequate diluent. Diluents preferably used are, for example, aliphatic, alicyclic and aromatic hydrocarbons (may be optionally chlorinated), such as, hexane, cyclohexane, petroleum ether, ligroine, benzene, toluene, xylene, methylene chloride, chloroform, carbon tetrachloride, ethylene chloride, chlorobenzene etc.; ethers, such as, diethyl ether, methyl ethyl ether, di-isopropyl ether, dibutyl ether, dioxane, tetrahydrofuran etc.; alcohols, such as, methanol, ethanol, isopropanol, butanol, ethylene glycol etc.; esters, such as, ethyl acetate, amyl acetate etc.; acid amides, such as, dimethylformamide, dimethylacetamide, N-methylpyrrolidone etc.; carboxylic acids, such as, formic acid, acetic acid etc.

When carrying out the process (a) according to the invention the reaction temperatures can be varied within a relatively wide range. In general, the process is carried out at temperatures between −20° C. and 100° C., preferably between 0° C. and 80° C. The process according to the invention is generally carried out under atmospheric pressure. However, it is also possible to carry out the process according to the invention under elevated or reduced pressure.

In preparation process (b) according to the invention, the compounds of the formula (I) can be obtained, for example, by reacting 0.8–3 moles of m-chloroperbenzoic acid with 1 mole of a compound of the formula (Ia) in a diluent, for example, methylene chloride at room temperature.

The reaction of the aforementioned preparation process c) can be conducted in the presence of an adequate diluent. Diluents preferably used are, for example, aliphatic, alicyclic and aromatic hydrocarbons (may be optionally chlorinated), such as, hexane, cyclohexane, petroleum ether, ligroine, benzene, toluene, xylene, methylene chloride, chloroform, carbon tetrachloride, ethylene chloride, chlorobenzene etc.; ethers, such as, diethyl ether, methyl ethyl ether, di-isopropyl ether, dibutyl ether, dioxane, tetrahydrofuran etc.; acid amides, such as, dimethylformamide, dimethylacetamide, N-methylpyrrolidone etc.; sulfones and sulfoxides, such as, dimethyl sulfoxide, sulfolane etc.

When carrying out the process (a) according to the invention the reaction temperatures can be varied within a relatively wide range. In general, the process is carried out at temperatures between −20° C. and 200° C., preferably between 0° C. and 150° C. The process according to the invention is generally carried out under atmospheric pressure. However, it is also possible to carry out the process according to the invention under elevated or reduced pressure.

In preparation process (a) according to the invention, the compounds of the formula (I) can be obtained, for example, by reacting 1–4 moles of N-chlorosuccinimide with 1 mole of a compound of the formula (Ib) in a diluent, for example, carbon tetrachloride under refluxing.

The compounds of the formula (I) of the present invention show a strong nematicidal activity. They can, therefore, be efficiently used as nematicidal agents, for example, in the field of agriculture and forestry. Remarkably, the compounds of the formula (I) of the present invention are not phytotoxic while at the same time effectively controlling harmful nematodes.

The compounds according to the invention can be used, for example, against nematodes such as *Pratylenchus* spp., *Globodera* spp., such as *Globodera rostochiensis wollenweber*, *Heterodera* spp., such as *Heterodera glycines ichinohe*, *Meloidogyne* spp., *Aphelenchoides* spp., such as *Aphelenchoides basseyi christie*, *Radopholus similis*, *Ditylenchus dipsaci*, *Tylenchulus seipenetrans*, *Longidorus* spp., *Xiphinema* spp., *Trichodorus* spp., *Bursaphelenchus* spp., such as *Bursaphelenchus xylophilis* etc.

The compounds according to the invention are especially useful for combating *Pratylenchus* spp., *Globodera rostochiensis wollenweber*, *Heterodera glycines ichinohe*, *Meloidogyne* spp., *Aphelenchoides basseyi christie*, *Bursaphelenchus xylophilis*.

However, the use of the active compounds according to the invention is in no way restricted to these genera, but also extends in the same manner to other nematodes.

The active compounds of the present invention can exist also as a mixed agent with other active compounds, for example, insecticides, bactericides, miticides, fungicides etc. in the form of their commercially useful formulation or in the application form prepared from those formulations. Here, as insecticides, there can be mentioned, for example, organophosphorous agents, carbamate agents, carboxylate type chemicals, chlorinated hydrocarbon type chemicals, chloronicotinyl type chemicals, insecticidal substances produced by microbes etc.

The active compounds according to the invention, as such or in their formulations, can also be used in a mixture with known fungicides, bactericides, acaricides, nematicides or insecticides, to widen, for example, the activity spectrum or to prevent the development of resistance. In many cases, this results in synergistic effects, i.e. the activity of the mixture exceeds the activity of the individual components. Such formulations and application forms are commercially and ecologically especially useful as generally lower amounts of active ingredients can be used. A synergist, however, must not necessarily be active itself, as long as it enhances the action of the active compound.

The content of the active compounds of the present invention in a commercially useful formulation or application form can be varied in a wide range. The active-compound content of the use forms prepared from the commercial formulations can vary within limits. The active-compound concentration of the use forms can be from 0.0000001 to 100% by weight of active compound, preferably between 0.0001 and 1% by weight.

Examples of particularly advantageous mixing components are the following:

Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutlanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, iso-prothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfoxuram, metiram, mretomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichloro-phenyl)-β-fluoro-b-propyl-1H-1,2,4-triazole-1-ethanol, α-(2,4-dichlorophenyl)-β-methoxy-a-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxy-imino)-N-methyl-2-phenoxy-phenylacetamide, isopropyl 1-{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone, O-(phenylmethyl) oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl thiocyanate, 2,6-dichloro-N-(4-trifluoromethylbenzyl)-benzamide, 2,6-dichloro-N-[[4(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-a-D-glucopyranlosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridine-carboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)-oxy]-methyl]-benzamide, 3-(1,1-dimethylpropyl-1-oko-1H-indene-2-carbonitrile, 3-[2-(4-chlorophenyl)-5-ethoxy-3-isoxazolidinyl]-pyridine, 4-chloro-2-cyano-N,N-dimethyl-5-(4-methyl-phenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl) 3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium hydrogen carbonate, methanetetrathiol sodium salt, methyl 1-(2,3- dihydro-2,2-dimethyl-1H-inden-1-yl)-1H-imidazole-5-carboxylate, methyl N-(2,6-dimethyl-phenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclo-hexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidineamine, N-(4-hexylphenyl)-1,4 5,6-tetrahydro-2-pyrimidineamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, and spiro[2H]-1-benzopyran-2,1'(3'H)-isobenzofuran]-3'-one.

Batericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricide/Nematicides abamectin, acephate, acetamiprid, acranathrin, alanycarb, aldicaarb aldoxycarb, alpha-cypermethrin, alphamethrin, amitraz, avermectin, AZ 60541, azadirachtin, azamethiphos, azinphos A, azinphos M, azocyclotin, *Bacillus popilliae, Bacillus sphaericus, Bacillus subtilis, Bacillus thuringiensis*, baculoviruses, *Beauveria bassiana, Beauveria tenella*, bendiocarb, beenfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrine demeton M, demeton S, demeton-S-methyl, diafenthiuron, diazinon, dichlorvos, diflubenzuron, dimethoat, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithin, fenpyroximate, fenvalerate, fipronil, fluazinamr, fluazuron, flubrocythinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hyprodrene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoat, oxamyl, oxydemethon M, *Paecilomyces funosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, suprofos, taufluvalinate, tebufenozide, tebufenpyrad, tebupirimiphos, teflubenzuron, tefluthrin, temephos, temivinphos, terbufos, tetrachlorvinphos, theta-cyperinethrin, thiamethoxam, thiapronil, thiatriphos, thiocyclarn hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamiudothion, vaniliprole, *Verticillium lecanii*, YI; 5302, zeta-cypermethrin, zolaprofos, (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl 2,2,3,3-tetramethyl-cyclopropanecarboxylate, 1-[(2-chloro-5-thiazolyl)methyl] tetrahydro-3,5-dimethyl-N-nitro-1,3,5-triazine-2(1H)-imine, 2-(2-chloro-6-fluorophenyl)-4-[4-(1,1-dimethyl-ethyl)phenyl]-4,5-dihydro-oxazole, 2-(acetlyoxy)-3-dodecyl-1,4-naphthalenedione, 2-chloro-N-[[[4-(1-phenylethoxy)-phenyl]-amino]-carbonyl]-benzamide, 2-chloro-N-[[[-(2,2-dichloro-1,1-difluoroethoxy)-phenyl]-amino]-carbonyl]-benzamide, 3-methylphenyl propylcarbamate, 4-[4-(4ethoxyphenyl)-4-methylpentyl]-1-fluoro-2-phenoxy-benzene, 4-chloro-2-(1,1-dimethylethyl)-5-[[2-(2,6-dimethyl-4-phenoxy-phenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, *Bacillus thuringienis* strain EG-2348, [2-benzoyl-1-(1,1-dimhethylethyl)-hydrazinobenzoic acid, 2,2-dimethyl-3-(2,4-dichlorophenyl)-2-oxo-1-oxaspiro[4.5]dec-3-en-4-yl butanoate, [3-[(6-chloro-3-pyridinyl)methyl]-2-thiazolidinylidene]-cyanamide, dihydro-2-(nitro-methylene)-2H-1,3-thiazine-3(4H)-carboxaldehyde, ethyl [2-[[1,6-dihydro-6-xo-1-(phenylmethyl)-4-pyridazinyl]oxy] ethyl]-carbamate, N-(3,4,4-trifluoro-1-oxo-3-butenyl)-glycine, N-(4-chlorophenyl)-3-[4-(difluoromethoxy)phenyl] 4,5-dihydro-4-phenyl-1H-pyrazole-1-carboxamide, N-[(2-chloro-5-thiazolyl)methyl]-N'-methyl-N''-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropyl-amino)-2-oxoethyl]-ethylphosphoroamidothioate.

A mixture with other known active compounds, such as herbicides, or with fertilizers and growth regulators is also possible.

The active compounds of the present invention can be converted into customary formulations such as solutions, emulsions, wettable powders, water-dispersible granules, suspensions, powders, foaming agents, pastes, granules, active compound-impregnated natural and synthetic substances, microcapsules, fumigants etc.

These formulations can be prepared according to per se known methods, for example, by mixing the active compounds with extenders, namely liquid, liquefied gas or solid diluents or carriers, and optionally with surface-active agents, namely emulsifiers and/or dispersants and/or foam-forming agents. If the extender used is water, it is also possible to use, for example, organic solvents as auxiliary solvents. Suitable liquid solvents are essentially: aromatics, such as xylene, toluene, or alkylnaphthalenes, chlorinated aromatics and chlorinated aliphatic hydrocarbons, such as chloro-benzene, chloroethylenes or methylene chloride, aliphatic hydrocarbons, such as cyclohexane or paraffis, for example mineral oil fractions, mineral or vegetable oil, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Liquid diluents or carriers can be, for example, aromatic-hydrocarbons (for example, xylene, toluene, alkylnaphthalene etc.), chlorinated aromatic or chlorinated aliphatic hydrocarbons (for example, chlorobenzenes, ethylene chlorides, methylene chloride etc.), aliphatic hydrocarbons (for example, cyclohexane etc. or paraits, such as, mineral oil fractions etc.), alcohols (for example, butanol, glycols and their ethers, esters etc.), ketones (for example, acetone, methyl ethyl ketone, methyl isobutyl ketone, cyclohexanone etc.), strongly polar solvents (for example, dimethylformamide, dimethyl sulfoxide etc.), water etc.

Liquefied gas diluents or carriers are liquefied substances which are gases at normal temperature and pressure. Liquefied gas diluents can be, for example, aerosol propellants such as butane, propane, nitrogen gas, carbon dioxide, halogenated hydrocarbons, etc.

Solid diluents can be, for example, ground natural minerals (for example, kaolin, clay, talc, chalk, quartz, attapulgite, montmorillonite, diatomaceous earth etc.), ground synthetic minerals (for example, highly dispersed silicic acid, alumina, silicates etc.) etc.

Solid carriers for granules can be, for example, crushed and fractionated rocks (for example, calcite, marble, pumice, sepiolite, dolomite etc.) synthetic granules of inorganic and organic meals, particles of organic materials (for example, saw dust, coconut shells, maize cobs, tobacco stalks etc.) etc.

Emulsifiers and/or foam-forming agents can be, for example, nonionic and anionic emulsifiers, for example, polyoxyethylene fatty acid esters, polyoxyethylene fatty acid alcohol ethers, such as, alylaryl polyglycol ethers, alkylsulfonates, alkylsulfates, arylsulfonates etc., albumin hydrolysis products etc.

Dispersants include, for example, lignin sulfite waste liquor, methyl cellulose etc.

Tackifiers can also be used in formulations (powders, granules, emulsifiable concentrates). As usable tackifiers there can be mentioned; for example, carboxymethyl cellulose, natural and synthetic polymers (for example, gum Arabic, polyvinyl alcohol, polyvinyl acetate etc.).

Colorants can also be used. Colorants can be, for example, inorganic pigments (for example, iron oxide, titanium oxide, Prussian Blue etc,), organic dyestuffs such as alizarin dyestuffs, azo dyestuffs or metal phthalocyanine dyestuffs, and further traces nutrients such as salts of metals such as iron, manganese, boron, copper, cobalt, molybdenum, zinc etc.

Said formulations can contain the aforementioned active components in a range of generally 0.1–95% by weight, preferably 0.5–90% by weight.

Then the preparations and applications of the compounds of the present invention will be described more specifically by the following examples. The present invention, however, should not be restricted to them in any way. "Parts" mean "parts by weight" unless specified.

EXAMPLES

Synthesis Example 1

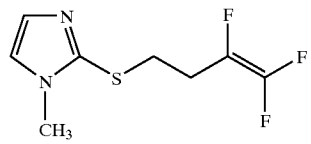

7.98 g (69.90 mmol) of 2-mercapto-1-methylimidazole, 10.6 g (76.69 mmol) of potassium carbonate and 14.6 g (77.26 mmol) of 4-bromo-1,1,2-trifluoro-1-butene were suspended in 70 ml of acetonitrile and refluxed for 6 hours. After filtering the precipitates, the filtrate was concentrated under reduced pressure and the residue was purified by column chromatography (dichloromethane: ethanol=99:1) to obtain 8.5 g of 1-methyl-2-(3',4',4'-trifluoro-3'-butenylthio)imidazole. $n_D^{20}$=1.4928, yield 37%.

Synthesis Example 2

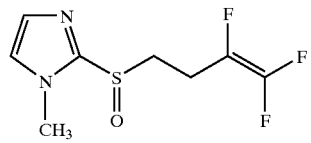

1 g (4.50 mmol) of 1-methyl-2-(3',4',4'-trifluoro-3'-butenylthio)imdazole was dissolved in 30 ml of dichloromethane, to which 1.1 g (6.30 mmol) of m-chloroperbenzoic acid (purity about 70%) was added little by little. After stirring at room temperature for 8 hours, it was washed with saturated sodium hydrogen carbonate and water and dried with anhydrous sodium sulfate. After the solvent was distilled off under reduced pressure, the residue was treated with column chromatography (dichloromethane: ethanol=19:1) to obtain 0.91 g of 1-methyl-2-(3',4',4'-trifluoro-3'-butenylsulfinyl)imidazole. $n_D^{20}$=1.5040, yield 85%.

Synthesis Example 3

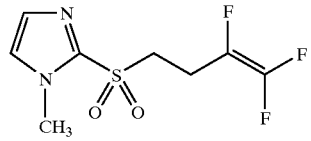

1 g (4.50 mmol) of 1-methyl-2-(3',4',4'-trifluoro-3'-butenylthio)imidazole was dissolved in 30 ml of dichloromethane, to which 2.17 g (12.57 mmol) of m-chloroperbenzoic acid (purity about 70%) was added little by little. After stirring at room temperature for 8 hours, it was washed with saturated sodium hydrogen carbonate and water and dried with anhydrous sodium sulfate. After the solvent was distilled off under reduced pressure, the residue was treated with column chromatography (dichloromethane: (ethanol=49:1) to obtain 0.83 g of 1-methyl-2-(3',4',4'-trifluoro-3'-butenylsulfonyl)imidazole. $n_D^{20}$=1.4819, yield.73%.

Synthesis Example 4

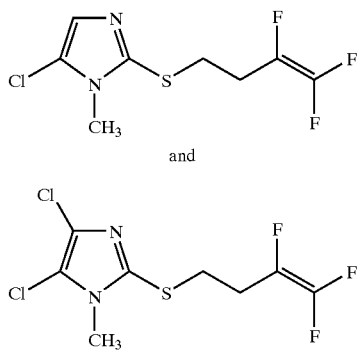

2.22 g (10 mmol) of 1-methyl-2-(3',4',4'-trifluoro-3'-butenylthio)imidazole was dissolved in 30 ml of-dichloromethane, to which 1.62 g (12 mmol) of suililryl chloride was added little by little drop by drop under ice cooling. After the addition and stirring at room temperature for 4 hours, 25 ml of saturated aqueous solution of sodium hydrogen carbonate was added and stirred for 30 minutes. The organic layer and aqueous layer were separated and the aqueous layer was extracted with dichloro methane.) The extract was put together with the organic layer. The total organic layer was washed with saturated aqueous solution of sodium chloride, dried with anhydrous sodium sulfate, and the solvent was distilled off under reduced pressure. The residue was treated with column chromatography (hexane: ethyl acetate=5:1) to obtain 0.93 g of 5-chloro-1-methyl-2-(3',4',4'-trifluoro-3'-butenylthio) imidazole ($n_D^{20}$=1.5170, yield 36%) and 0.2 g of 4,5-dichloro-1-methyl-2-(3',4',4'-trifluoro-3'-butenylthio) imidazole. $n_D^{20}$=1.5029, yield 7%.

Synthesis Example 5

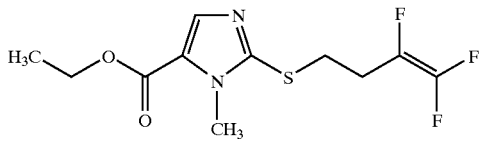

6 g (21.41 mmol) of 4-ethoxycarbonyl-2-(3',4',4'-trifluoro-3'-butenylthio)imidazole, 3.25 g (23.5 mmol) of potassium carbonate and 2.96 g (23.47 mmol) of dimethyl sulfate were suspended in 60 ml of acetonitrile and refluxed for 4 hours. After cooling and filtering the precipitates, the filtrate was concentrated under reduced pressure and the residue was treated by column chromatography (dichloromethane: ethanol=99:1) to obtain 2.1 g of 5-ethoxycarbonyl-1-methyl-2-(3',4',4'-trifluoro-3'-butenylthio)imidazole. $n_D^{20}$=1.5013, yield 33%.

The compounds of the formula (I) of the present invention, which can be synthesized by processes similar to the above-mentioned Synthesis Examples 1–5 are shown the following Table 1. The compounds obtained in Synthesis Examples 1–5 are also shown in Table 1.

In Table 1, Me represents methyl, Et represents ethyl, n-Pr represents n-propyl, iso-Pr represents isopropyl, n-Bu represents n-butyl, sec-Bu represents sec-butyl, tert-Bu represents tert-butyl cy-Pr represents cyclopropyl, cy-Pen represents cyclopentyl, cy-Hex represents cyclohexyl, and Ph represents phenyl.

TABLE 1

| Compound No | $R^1$ | $R^2$ | $R^3$ | n | mp. [° C.]/$n_{20}^D$ |
|---|---|---|---|---|---|
| 1 | H | H | Me | 0 | 1.4928 |
| 2 | H | H | Me | 1 | 1.5040 |
| 3 | H | H | Me | 2 | 1.4819 |
| 4 | H | H | Et | 0 | 1.4802 |
| 5 | H | H | Et | 1 | |
| 6 | H | H | n-Pr | 0 | 1.4849 |
| 7 | H | H | n-Pr | 1 | |
| 8 | H | H | n-Pr | 2 | |
| 9 | H | H | iso-Pr | 0 | 1.4830 |
| 10 | H | H | iso-Pr | 1 | |
| 11 | H | H | n-Bu | 0 | |
| 12 | H | H | n-Bu | 1 | |
| 13 | H | H | sec-Bu | 0 | 1.4795 |
| 14 | H | H | sec-Bu | 1 | 1.4832 |
| 15 | H | H | sec-Bu | 2 | |
| 16 | H | H | tert-Bu | 0 | 1.4830 |
| 17 | H | H | tert-Bu | 1 | |
| 18 | H | H | n-Pen | 0 | |
| 19 | H | H | cy-Pr | 0 | 1.4928 |
| 20 | H | H | cy-Pr | 1 | |
| 21 | H | H | cy-Pen | 0 | |
| 22 | H | H | cy-Hex | 0 | |
| 23 | H | H | $CH_2$=$CHCH_2$ | 0 | 1.4960 |
| 24 | H | H | MeCH=$CHCH_2$ | 0 | |
| 25 | H | H | $PhCH_2$ | 0 | 1.5435 |
| 26 | H | Cl | Me | 0 | 1.5170 |
| 27 | H | Cl | Me | 1 | 1.5018 |
| 28 | H | Cl | Me | 2 | |
| 29 | H | Cl | Et | 0 | |
| 30 | H | Cl | Et | 1 | |
| 31 | H | Cl | n-Pr | 0 | |
| 32 | H | Br | Me | 0 | |
| 33 | H | Br | Me | 1 | |
| 34 | H | MeOCO | Me | 0 | |
| 35 | H | EtOCO | H | 0 | 36–41 |
| 36 | H | EtOCO | Me | 0 | 1.5013 |
| 37 | H | EtOCO | Me | 1 | |
| 38 | H | n-PrOCO | Me | 0 | |
| 39 | Cl | Cl | Me | 0 | 1.5029 |
| 40 | Cl | Cl | Me | 1 | 60–61 |
| 41 | Cl | Cl | Me | 2 | 77–78 |
| 42 | Cl | Cl | Et | 0 | |
| 43 | Br | Br | Me | 0 | |
| 44 | Br | Br | Me | 1 | |
| 45 | Cl | EtOCO | Me | 0 | 1.5122 |
| 46 | Cl | EtOCO | Me | 2 | |

Synthesis Reference Example (Intermediate)

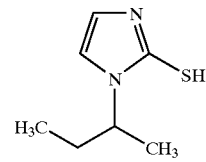

1 g (9.89 mmol) of 2-mercaptooxazole and 0.72 g (9.89 mmol) of sec-butylamine were dissolved in 20 ml of ethanol and refluxed for 2 hours. After cooling, the solvent was distilled off under reduced pressure and the residue was treated with column chromatography to obtain 0.83 g of 1-sec-butyl-2-mercaptoimidazole. mp.=108–121° C., yield 54%.

Use Example 1
Test Against *Meloidogyne* spp). (Soil Pot Test)

Preparation of Test Agent: 1 part of the active compound is impregnated to 99 parts of pumice to produce fine granules.

The test agent prepared as mentioned above was added to the soil contaminated with *Meloidogyne incognita* to provide for a concentration of 10 ppm of the active ingredient. The soil and the test agent were homogeneously mixed by stirring and a pot (1/5000 are) was filled with the soil. About 20 seeds of tomato (variety: Kurihara) were sown per pot. After cultivation in a greenhouse for 4 weeks, they were carefully pulled out not to-damage the roots and the root knot index and the controlling effect were determined as follows:

Degree of damage 0: No knots were formed (Complete control)
1: A few knots were formed.
2: Knots were formed to a medium extent.
3: Knots were formed to an intense extent.
4: Knots were formed to the most intense extent (which corresponds to non-treatment).

$$\text{Root knot index} = \frac{\Sigma(\text{degree of damage} \times \text{number of individuals})}{\text{Total number of tested individuals} \times 4} \times 100$$

The controlling effect of the compounds tested can then be evaluated according to the following equation:

$$\text{Controlling effect [\%]} = \frac{(\text{Root knot index at non-treated area}) - (\text{Root knot index at treated area})}{\text{Root knot index at non-treated area}} \times 100$$

In the test described, the following compounds showed more than 90% controlling effect at an effective concentration of 10 ppm: Compounds No. 2 and 3.

Formulation Examples

Example 1 (Granule)

To a mixture of 10 parts of the compound of the present invention (Ex. 2), 30 parts of bentonite (montmorillonite), 58 parts of talc and 2 parts of ligninsulfonate salt, 25 parts of water were added, well kneaded, made into granules of 10–40 mesh by an extrusion granulator and dried at 40–50° C. to obtain granules.

Example 2 (Granules)

95 Parts of clay mineral particles having particle diameter distribution of 0.2–2 mm are submitted to a rotary mixer. While rotating it, 5 parts of the compound of the present invention (No. 3) are sprayed together with a liquid diluent, wetted uniformly and dried at 40–50° C. to obtain granules.

Example 3 (Emulsifiable Concentrate)

30 Parts of the compound of the present invention (Ex. 2), 55 parts of xylene, 8 parts of polyoxyethylene alkyl phenyl ether and 7 parts of calcium alkylbenzenesulfonate were mixed and stirred to obtain an emulsifiable concentrate.

Example 4 (Wettable Powder)

15 Parts of the compound of the present invention (Ex. 3), 80 parts of a mixture of white carbon (hydrous amorphous silicon oxide fine powders) and powder clay (1:5), 2 parts of sodium alkylbenzenesulfonate and 3 parts of sodium alkylnaphthalenesulfonate-formalin-condensate were crushed and mixed to produce a wettable powder.

What is claimed is:

1. A compound of formula (I)

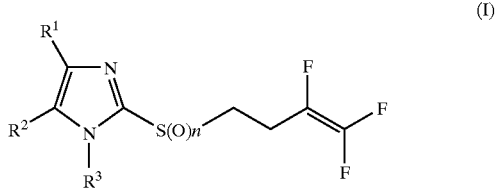

(I)

wherein $R^1$ represents hydrogen or halogen, $R^2$ represents hydrogen, halogen, or alkoxycarbonyl, $R^3$ represents hydrogen, alkyl, alkenyl, cycloalkyl, or aralkyl, and n represents 0, 1, or 2, with the proviso that $R^1$, $R^2$, and $R^3$ do not all represent hydrogen at the same time.

2. A compound of formula (I) according to claim 1 wherein $R^1$ represents hydrogen, fluoro, chloro, or bromo, $R^2$ represents hydrogen, fluoro, chloro, bromo, methoxycarbonyl, ethoxycarbonyl, n- or i-propoxycarbonyl, or n-, i-, s-, or t-butoxycarbonyl, and $R^3$ represents hydrogen, $C_{1-6}$-alkyl, $C_{3-4}$-alkenyl, $C_{3-6}$-cycloalkyl or benzyl.

3. A compound of formula (I) according to claim 1 wherein $R^1$ represents hydrogen, chloro, or bromo, $R^2$ represents hydrogen, chloro, bromo, methoxycarbonyl, ethoxycarbonyl, or n-propoxycarbonyl, and $R^3$ represents hydrogen, methyl, ethyl, n-propyl, isopropyl, n-butyl, sec-butyl, tert-butyl, n-pentyl, allyl, 2-butenyl, cyclopropyl, cyclopentyl, cyclohexyl, or benzyl.

4. A process for preparing compounds of formula (I) according to claim 1 comprising (a) for compounds of formula (I) in which n is 0, reacting a compound of formula (II)

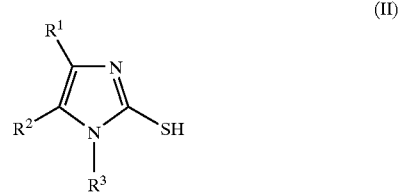

(II)

wherein $R^1$, $R^2$, and $R^3$ are as defined for formula (I) in claim 1, with 4-bromo-1,1,2-trifluoro-1-butene in the presence of inert solvents, and optionally in the presence of an acid binder, to form a compound of formula (Ia)

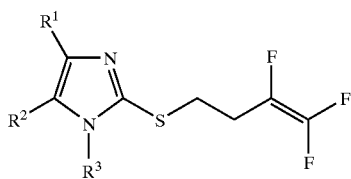 (Ia)

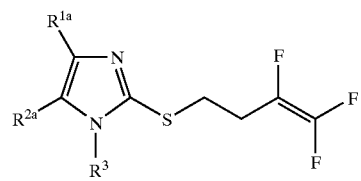 (Ib)

wherein $R^1$, $R^2$, and $R^3$ are as defined for formula (I) in claim 1, and (b) for compounds of formula (I) in which n is 1 or 2, oxidizing the compound of formula (Ia) in the presence of an inert solvent.

5. A process for preparing a compound of formula (I) according to claim 1 in which $R^1$ represents hydrogen or halogen, $R^2$ represents halogen, and n represents 0, comprising reacting a compound of formula (Ib)

wherein
$R^{1a}$ and $R^{2a}$ each represent hydrogen, and
$R^3$ represents hydrogen, alkyl, alkenyl, cycloalkyl, or aralkyl, with a halogenating agent in the presence of an inert solvent.

6. A nematicidal composition comprising one or more compounds of formula (I) according to claim 1 and one or more extenders.

7. A method of combating nematodes comprising allowing an effective amount of one or more compounds of formula (I) according to claim 1 to act on nematodes and/or their habitat.

* * * * *